United States Patent [19]

Shibata et al.

[11] Patent Number: 4,582,657

[45] Date of Patent: Apr. 15, 1986

[54] METHOD OF MANUFACTURING ELECTROCHEMICAL CELL

[75] Inventors: Kazuyoshi Shibata; Yoshihiko Mizutani, both of Nagoya, Japan

[73] Assignee: NGK Insulators, Ltd., Nagoya, Japan

[21] Appl. No.: 751,323

[22] Filed: Jul. 2, 1985

[30] Foreign Application Priority Data

Jul. 6, 1984 [JP] Japan .................. 59-140347

[51] Int. Cl.[4] ............ B32B 31/00; G01N 27/46; B05D 5/12
[52] U.S. Cl. ................... 264/40.6; 204/426; 204/429; 204/425; 264/40.1; 264/44; 264/61; 427/124; 427/125; 427/126.2; 427/126.3; 427/126.4
[58] Field of Search .......... 204/15, 421–429; 264/40.1, 40.6, 61, 44; 427/123–125, 126.1, 126.2, 126.3, 126.4

[56] References Cited

U.S. PATENT DOCUMENTS

| | | | |
|---|---|---|---|
| 4,136,000 | 1/1979 | Davis et al. | 204/427 |
| 4,169,777 | 10/1979 | Young et al. | 204/427 |
| 4,186,071 | 1/1980 | Romine et al. | 204/427 |
| 4,294,668 | 10/1981 | Young | 204/424 |
| 4,514,812 | 4/1985 | Miller et al. | 264/40.1 |

Primary Examiner—T. Tung
Attorney, Agent, or Firm—Parkhurst & Oliff

[57] ABSTRACT

A method of manufacturing an electrochemical cell for determining the cencentration of a component of a measurement gas, which comprises a solid electrolyte body, and a pair of electrodes which are disposed on the solid electrolyte body and spaced apart from each other, such that one of the electrodes is exposed to the measurement gas via a porous ceramic diffusion layer having a predetermined diffusion resistance to the component of the measurement gas, so that an atmosphere adjacent to the above one electrode is controlled by means of reaction of the pair of electrodes by application of an electric current thereto, the method comprising the steps of: preparing an unfired or calcined laminar structure of the electrochemical cell such that an unfired or calcined layer of the above one electrode is covered by an unfired or calcined layer of the porous ceramic diffusion layer; starting a firing process to fire the laminar structure at predetermined elevated temperatures; applying an electric voltage or current to the electrodes; and terminating the firing process when a value of current flowing through the electrodes or a value of voltage present between the electrodes has become equal to a predetermined value at which is obtained a desired rate of diffusion of the gas component to the above one electrode through the porous ceramic diffusion layer.

4 Claims, 13 Drawing Figures

METHOD OF MANUFACTURING ELECTROCHEMICAL CELL

BACKGROUND OF THE INVENTION

1. Field of the Art

The present invetion relates generally to a method of manufacturing an electrochemical cell, and more particularly to an improved method of manufacturing electrochemical cells with an improved consistency in quality, which use solid electrolyte for determining or measuring the concentration of a component of a gas.

2. Related Art Statement

There have been known various electrochemical devices, each of which comprises at least one electrochemical cell using a solid electrolyte body. Such electrochemical devices are used, for example, as oxygen sensors to detect the oxygen concentration of an exhaust gas from internal combustion engines of automotive vehicles. Typical examples of such oxygen sensors include an oxygen sensor which employs a mass of oxygen-ion conductive solid electrolyte such as zirconia ceramics, to determine the oxygen concentration according to the principle of an oxygen concentration cell. Also known in the art are electrochemical devices or elements which are used as sensors or detectors for hydrogen, nitrogen, carbon dioxide, etc. In the field of producing such electrochemical devices, there has been an increasing trend of using an electrochemical cell of laminar structure which comprises a planar solid electrolyte body and planar electrodes disposed in contact with a surface or surfaces of the planar body of solid electrolyte.

In the production of such electrochemical cells, a diffusion layer having a predetermined diffusion resistance to molecules of a measurement gas is formed on a body of zirconia ceramics or other solid electrolyte so as to cover an electrode which is disposed on the solid electrolyte body for exposure to an external measurement gas, so that the atmosphere contacting the electrode is controlled by the diffusion layer covering the electrode. It is also known that a pair of electrodes are disposed on opposite sides of such a diffusion layer so that the diffusion layer functions as a solid electrolyte body through which the pumping current flows by application of a pumping current to the two electrodes. In either case, the electrochemical cell for determining the concentration of a given component of a measurement gas, comprises a solid electrolyte body, and at least one pair of electrodes which are disposed on the solid electrolyte body and spaced apart from each other, such that at least one of the pair of electrodes is exposed to the measurement gas via a porous ceramic diffusion layer having a predetermined diffusion resistance to molecules of the component of the measurement gas, so that the atmosphere adjacent to the above-identified at least one electrode is controlled by means of reaction at the at least one pair of electrodes by application of an electric current thereto.

The porous ceramic diffusion layer of the electrochemical cell indicated above may be formed, for example, by firing an unfired or calcined layer of suitable material, together with unfired or calcined layers of other members of the electrochemical cell, so that a laminar structure including the porous ceramic diffusion layer is co-fired. Alternatively, the porous ceramic diffusion layer may be formed by melting spinel or similar material by a plasma flame and spraying the molten material on the layer of the solid electrolyte.

PROBLEM ENCOUNTERED IN THE ART

However, when the electrochemical cells are manufactured in batch, their porous ceramic diffusion layers tend to have a considerable variation in diffusion resistance from one to another. In other words, it has been considered difficult to produce electrochemical cells of uniform quality whose porous ceramic diffusion layers have substantially the same value of diffusion resistance. More particularly, the diffusion resistance of porous ceramic diffusion layers are greatly affected by their thickness and their area of contact with the electrode, even when the diffusion layers are made of the same material. Further, the porosity of the ceramic diffusion layers is affected by the specific firing temperatures and other firing conditions. Accordingly, the porous ceramic diffusion layers of the different electrochemical cells have different values of diffusion resistance due to differences in thickness thereof, area of contact with the electrode and firing conditions.

In industrial production of electrochemical cells having the porous ceramic diffusion layers discussed above, it is of prime importance to form the ceramic diffusion layers with a uniform diffusion resistance on all electrochemical cells, in order to assure consistency in quality. However, it has been difficult to form the ceramic diffusion layers with uniform thickness, and with uniform area of contact with the corresponding electrode, while maintaining an industrially justified high level of productivity. In the case where a large number of electrochemical cells are fired in a furnace, it is considered difficult to solve the conventionally experienced inconvenience that the cells at different locations within the furnace are fired at different temperatures.

SUMMARY OF THE INVENTION

It is therefore an object of the present invention to solve the foregoing problems encountered in the known methods of producing electrochemical cells.

To attain the above object, there is provided according to the invention a method of manufacturing an electrochemical cell for determining the concentration of a given component of a measurement gas, which has a solid electrolyte body, and at least one pair of electrodes which are disposed on the solid electrolyte body and spaced apart from each other, such that at least one of the pair of electrodes is exposed to the measurement gas via a porous ceramic diffusion layer having a predetermined diffusion resistance to molecules of the component of the measurement gas, so that an atmosphere adjacent to the above-identified at least one electrode is controlled by means of reaction at the at least one pair of electrodes by application of an electric current thereto, comprising the steps of: preparing an unfired or calcined laminar structure of the electrochemical cell such that an unfired or calcined layer of the above-identified at least one electrode is covered by an unfired or calcined layer of the porous ceramic diffusion layer; starting a firing process to fire the unfired or calcined laminar structure at predetermined elevated temperatures; applying an electric voltage or current to said at least one pair of electrodes; and terminating said firing process when a value of current flowing through, or voltage present between, the pair of electrodes has become equal to a predetermined value at which is obtained a desired rate of diffusion of the component of the measurement gas through the porous ceramic diffusion layer to said at least one electrode.

In the method of manufacturing an electrochemical cell according to the invention, the variation in diffusion rate of the gas component through the porous ceramic diffusion layer of the cell under firing process is detected by monitoring a value of electric voltage or current applied to the electrodes while the firing of the porous ceramic diffusion layer is in progress. By terminating the firing operation of the individual electrochemical cells when the current or voltage has reached the predetermined value, the diffusion resistance of their porous ceramic diffusion layers, which is affected by their thickness and porosity, their area of contact with the corresponding electrode, and by other characteristics, may be adjusted to an optimum level, irrespective of differences in the characteristics of the diffusion layers of the individual electrochemical cells. Hence, the variation in diffusion resistance of the porous ceramic diffusion layers from one cell to another is reduced to an appreciable extent.

BRIEF DESCRIPTION OF THE DRAWING

The foregoing and other objects, features and advantages of the present invention will become more apparent from reading the following detailed description of preferred embodiments of the invention, when considered in conjunction with the accompanying drawing, in which.

DETAILED DESCRIPTION OF THE PREFERRED EMBODIMENTS

To further clarify the concept of the present invention, preferred embodiments of the invention will be described in detail referring to the accompanying drawing.

Figure 1A:
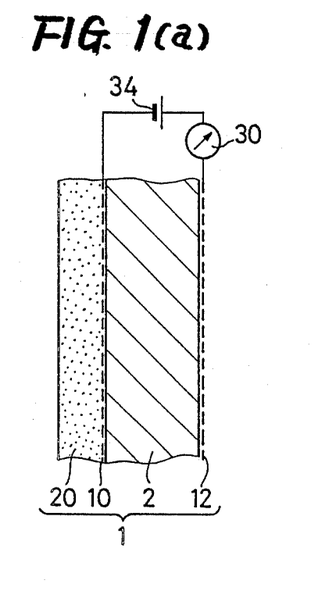
FIGS. 1(a) and 1(b) are fragmentary schematic views in cross section of basic arrangements of an electrochemical cell manufactured according to the invention.

An example of a basic arrangement of an electrochemical element or cell 1 which is manufactured according to a method of the invention is shown in FIG. 1(a), wherein reference numeral 2 designates layer of solid electrolyte. On opposite surfaces of the solid electrolyte layer 2, there are disposed a pair of electrodes 10, 12. A porous ceramic layer 20 is formed on the solid electrolyte layer 2 so as to cover the electrode 10.

In producing the electrochemical cell 1, the solid electrolyte layer 2, electrodes 10, 12 and porous ceramic layer 20 are formed, for example, as described below:

100 parts by weight of powder mixture consisting of 97 mole % of $ZrO_2$ and 3 mole % of $Y_2O_3$ are mixed with 1 part by weight of clay as a sintering agent or aid, 8 parts by weight of polyvinyl butyral resin as a binder, and 4 parts by weight of dioctyl phthalate as a plasticizer. A green sheet for the solid electrolyte layer 2 is prepared from the obtained mixture. Also, a paste for the electrodes 10, 12 is prepared by adding 6 parts by weight of polyvinyl butyral, 3 parts by weight of dibutyl phthalate and 50 parts by weight of butyl carbitol acetate, to 100 parts by weight of powder mixture which consists of 85% by weight of platinum and 15% by weight of zirconia. By using the prepared paste, unfired layers of the electrodes 10, 12 are screen-printed on the corresponding opposite surfaces of the green sheet of the solid electrolyte layer 2. Further, a paste for the porous ceramic layer 20 is prepared by adding 15 parts by weight of polyvinyl butyral, 8 parts by weight of dioctyl phthalate and 70 parts by weight of butyl carbaitol acetate, to 100 parts by weight of powder mixture which consists of 97% by weight of $Al_2O_3$ and 3% by weight of MgO. With the thus prepared paste, an unfired layer of the porous ceramic layer 20 is screen-printed on the appropriate surface of the green sheet of the solid electrolyte layer 2, such that the unfired layer of the electrode 10 is covered by the unfired layer of the porous ceramic layer 20. Thus, an unfired laminar structure of the cell 1 is formed.

The unfired laminar structure is calcined in air at 1380° C. for two hours, into a calcined laminar structure which comprises the gastight solid electrolyte layer 2, porous platinum electrodes 10, 12 and porous ceramic layer 20.

Subsequently, the calcined laminar structure of the electrochemical cell 1 is heated in the air to 1400° C., and the electrodes 10, 12 are connected to a DC-0.5 V power source 34. During the firing of the laminar structure, the value of a limiting current is measured by an ammeter 30, to detect an amount of oxygen which diffuses through the porous ceramic layer 20 to the electrode 10. As the calcined porous ceramic layer 20 is fired, its diffusion resistance to molecules of oxygen is increased, whereby the limiting current flowing through the electrodes 10, 12 is reduced as shown in FIG. 2(a).

Figure 2A:
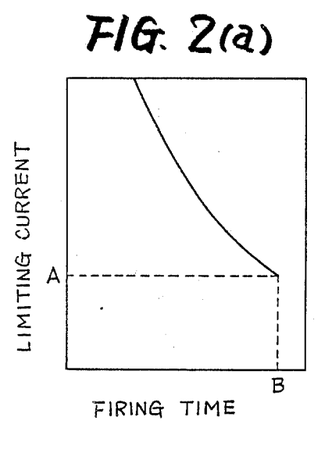
FIG. 2(a) is a graph showing an example of a curve representing a relation between a limiting current of a porous ceramic diffusion layer of the electrochemical cell during firing thereof, and a firing time of the diffusion layer.

In the method of the invention, the heating or firing operation of the calcined laminer structure of the electrochemical cell (porous ceramic layer 20, in particular) is stopped or terminated at a point of time "B" of FIG. 2(a), that is, when the limiting current has been lowered to a level "A". With the firing operation terminated at that point of time "B", the electrochemical cell 1 is formed with the porous ceramic layer 20 which has a predetermined diffusion resistance to molecules of oxygen in the air.

Figure 2B:
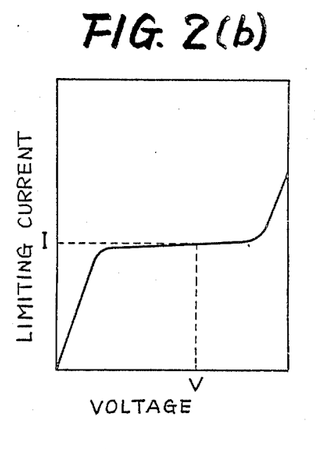
FIG. 2(b) is a graph showing a voltage-current curve of electrodes of the cell.

Instead of terminating the firing operation when the limiting current has been lowered to the predetermined level "A", it is possible to determine the required length of the firing time based on a predetermined level of voltage between the electrodes 10, 12, at which the porous ceramic layer 20 provides a desired diffusion resistance. FIG. 2(b) shows a current-voltage curve obtained by applying a current to the electrodes 10, 12 of a cell having a diffusion layer. In the figure, character "I" represents limiting current, while character "V"

represents voltage corresponding to the limiting current.

In brief, a desired value of the diffusion resistance of the porous ceramic layer 20 may be obtained by terminating the firing operation when either the current "I" or the voltage "V" has become equal to a predetermined level.

Figure 1B:
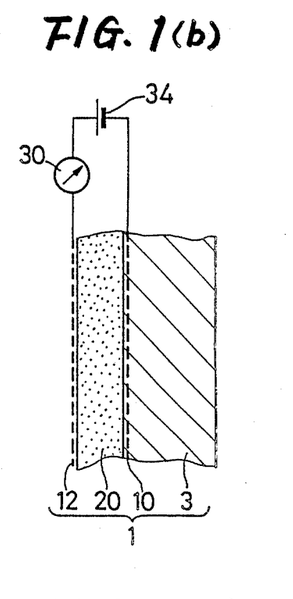

The electrochemical cell 1 which is manufactured according to the invention is not confined to the arrangement illustrated in FIG. 1(a), but may be otherwise arranged, provided one of a pair of electrodes disposed in contact with a solid electrolyte layer of the cell is exposed to a measurement gas via a porous ceramic diffusion layer. For example, the electrochemical cell 1 may take a basic arrangement as shown in FIG. 1(b) wherein the electrodes 10, 12 are disposed on opposite surfaces of the porous ceramic layer 20 which is made of a solid electrolyte material, while a gastight ceramic substrate 3 is formed on the porous ceramic layer 20 such that the gastight ceramic substrate 3 and the porous ceramic layer 20 cooperate to sandwich the electrode 10.

Figure 3:
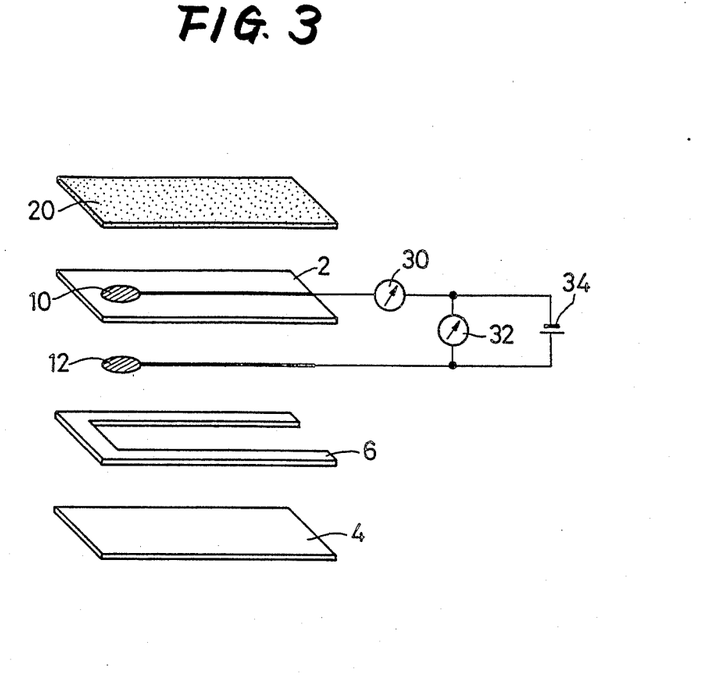
FIGS. 3, 4 and 5 are exploded perspective views of different arrangements of an electrochemical cell manufactured according to the method of the invention.
Figure 4:
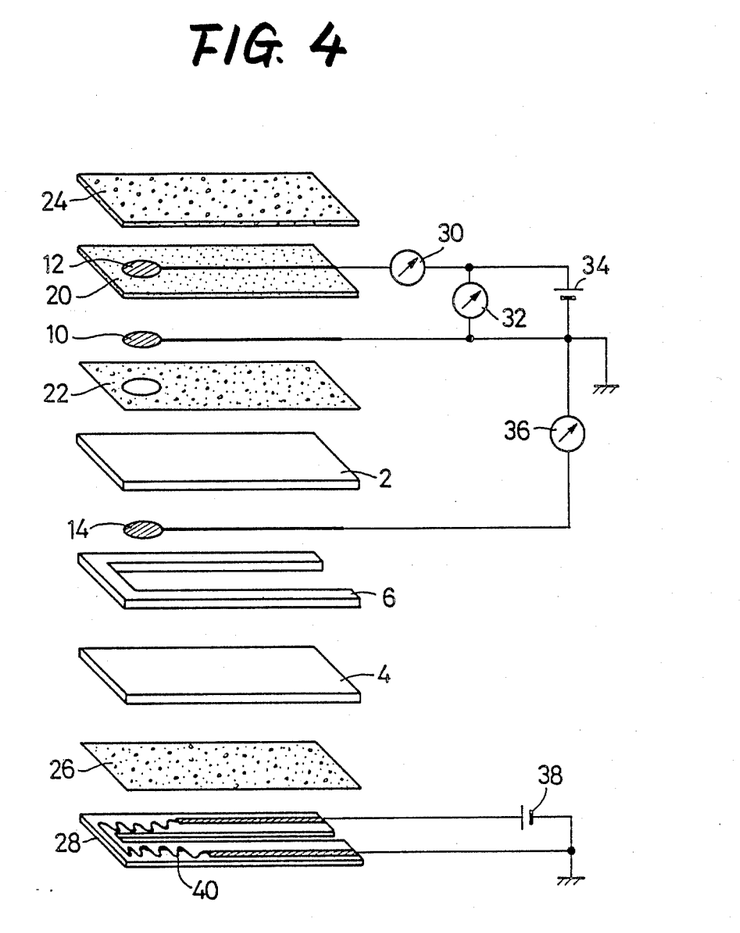
Figure 5:
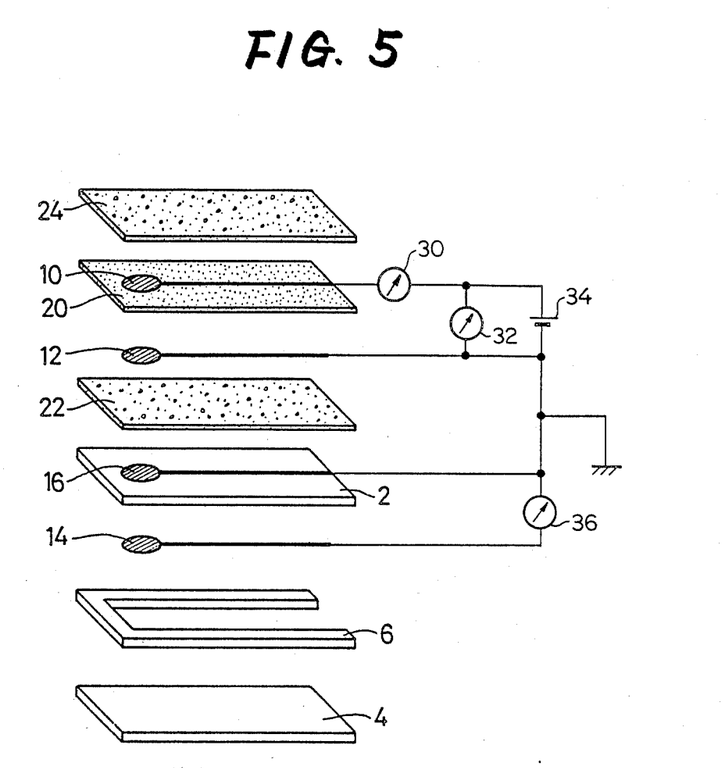

Examples of detailed construction of the electrochemical cell with the foregoing basic arrangements are illustrated in FIGS. 3–5. The method of the invention may be used to manufacture these different types of cells. In the construction of FIG. 3, the electrode 12 which is not covered by the porous ceramic layer 20 is exposed to the ambient air. More specifically, a U-shaped spacer 6 and an adjacent covering plate 4 cooperate to form a space which communicates with the atmosphere. The electrode 12 on the solid electrolyte layer 2 is located in the space for exposure to the air in the space. In the construction of FIG. 4, the electrodes 10, 12 are disposed on opposite surfaces of the porous ceramic layer 20 which serves as a solid electrolyte layer, so that the electrodes 10, 12 perform a pumping action. In operation, the potential of the electrode 10 covered by the porous ceramic layer 20 with a predetermined diffusion resistance to the measurement gas is compared with the potential of a reference electrode 14 which is exposed to the ambient air. The reference electrode 14 is disposed on the surface of the solid electrolyte layer 2 on the side remote from the porous ceramic layer 20. With the comparison of the potentials of the electrodes 10 and 14, the atmosphere surrounding the electrode 10 is detected. In this electrochemical cell, an electrical heater 40 is provided for maintaining the electrodes at a suitable operating temperature even while the temperature of the measurement gas is low, so that the cell may always be operated with high sensing accuracy and reliability. In the construction of FIG. 5, a pumping cell and a sensing cell are separated by an electrically insulating layer 22 which is interposed between the two cells. The pumping cell consists of the porous ceramic layer 20 made of solid electrolyte, and the electrodes 10, 12 disposed on the opposite surfaces of the porous solid electrolyte layer 20. The sensing cell consists of the solid electrolyte layer 2 of gastight structure, and the electrodes 14, 16 disposed on the opposite surfaces of the gastight solid electrolyte layer 2.

According to the instant method of the invention, the solid electrolyte which forms a substantive part of the electrochemical cell may be oxygen-ion conductive materials such as zirconia ceramics, solid solution of $Bi_2O_3$—$Y_2O_3$, proton-conductive materials such as $SrCe_{0.95}Yb_{0.05}O_{3-\alpha}$, or halogen-conductive materials such as $CaF_2$.

The component of a measurement gas which is sensed by the electrochemical cell, is not limited to elements which move as ions through a solid electrolyte material, but may be a substance which undergoes reaction with such elements. For example, if an electrochemical cell uses a solid electrolyte layer made of zirconia ceramics, it is possible to determine the concentration of hydrogen, carbon monoxide, hydrocarbon, etc. by reversing the direction of flow of a current applied to the electrodes. In this case, the hydrogen, carbon monoxide or hydrocarbon which has diffused through the porous ceramic layer reacts with oxygen produced at the electrode. As a result of the reaction, these components substantially completely disappear, and the voltage between the electrodes is abruptly changed. The concentration of the components may be detected by measuring a current at the time of the abrupt change in the voltage.

The porous ceramic layer may be made of a mass of particles of silica, alumina, spinel, zirconia, zircon, alkaline earth titanate, or zirconate. If necessary, known sintering agents or aids such as clay, or alkaline earth oxides may be added to the mass of such ceramic particles. Further, it is possible to add to the mass of particles suitable materials which will disappear at elevated temperatures, such as carbon particles, organic binders or wood chips.

Various known processes may be used to form the porous ceramic layer by using the above-indicated materials. The processes available include: forming a green sheet on the appropriate surface of a laminar structure of the cell under manufacture; immersing the laminar structure in a bath of a prepared slurry; screen-printing on the appropriate surface of the laminar structure, with a prepared paste; spraying the prepared slurry over the appropriate surface of the laminar structure; and electrostatic painting with the prepared material. The formation of the porous ceramic layer may be attained by using other techniques such as CVD, sputtering, and plasma spraying.

In the case where the basic arrangement of FIG. 1(a) is employed, it is not a prerequisite that the electrode 10 be disposed in close contact with the surface of the porous ceramic layer 20. Rather, it is possible to provide a suitable gap between the electrode 10 and the porous ceramic layer 20, for the purpose of avoiding uneven distribution of the component of the measurement gas over the surface of the electrode 10.

The electrodes 10, 12 may be made of metals such as platinum, rhodium, palladium, gold and nickel, or electrically conductive compounds of stannic oxides. Various methods may be used to form the electrodes. For example, a slurry is prepared from the above-indicated metallic material mixed with suitable ceramic particles, and the prepared slurry is applied by coating, screen-printing or spraying. The formed unfired layers are then fired into cermet electrodes. Alternatively, the electrodes may be formed in a plating, sputtering or CVD process, or by means of thermal decomposition of an aqueous solution of the material.

An unfired laminar structure of the electrochemical cell which is formed of the above-indicated materials in the suitable processes, is heated to form a fired laminar structure of the cell. For example, a laminar structure of green sheets of the cell components is first calcined until electric leads connected to the electrodes are given a physical strength sufficient for electrical connection with a power source. Alternatively, an unfired layer of solid electrolyte is completely fired. Subsequently, unfired layers of electrodes are formed on the fired layer of the solid electrolyte by plating or other methods, and an unfired layer for the porous ceramic layer is screen-printed with a prepared paste.

The calcined or unfired layer for the porous ceramic layer is then finally fired at a low rate. In the case where the laminar structure of green sheets is calcined, the final firing of the porous ceramic layer is generally effected at an optimum temperature at which the green sheet laminar structure was calcined. Alternatively, the previously calcined layer for the porous ceramic layer is finally fired at a constant temperature higher than the calcination temperature, or at a temperature which is gradually elevated from the calcination temperature level.

Generally, the calcination and/or firing at a suitably controlled temperature is achieved by external heating means. However, it is possible to use an electrical heater built in the cell, as auxiliary heating means. In this instance, the external heating means or the built-in heater may be used for adjusting the calcination or firing temperatures.

As previously described, the diffusion resistance of the porous ceramic layer under firing is detected by measuring a value of electric current while a predetermined voltage is applied between the electrodes. However, it is possible to terminate the firing operation when the voltage has become a predetermined level while the electric current is maintained at a constant level. For detecting the value of diffusion resistance of the porous ceramic layer, the electric current may be applied continuously or intermittently at desired time intervals. In either case, the value of electric current or voltage is measured while the electrodes are energized. It is noted that the measurement of the electric current or voltage need not be done while a firing or heating operation on the porous ceramic layer is in progress. That is, the firing or heating process may be interrupted for a suitable length of time, during which electric current or voltage is applied for detecting the diffusion resistance of the porous ceramic layer to a given component of the measurement gas at a temperature lower than the firing or heating temperature. In this case, the current or voltage is measured two or more times, each during the interruption of the heating operation, until the predetermined value has been obtained. However, it is possible that a point of time at which the predetermined diffusion resistance is reached be estimated based on a curve defined by the detected values of electric voltage or current. The firing operation is continued until the estimated point of time is reached. In other words, the timing at which the firing operation is terminated is determined based on the current-time or voltage-time curve obtained by measuring the current or voltage two or more times.

The porous ceramic layer thus fired is given a suitable degree of porosity that provides a diffusion resistance required for the electrochemical cell. The optimum porosity for the desired diffusion resistance is affected by the specific process in which the porous ceramic layer is formed. If the porous ceramic layer is formed by firing a green sheet, the porosity is preferably held within a range of approx. 2–30% as measured according to a method of mercury penetration porosimetry. If a plasma spraying process is used to manufacture the porous ceramic layer, the preferred range of porosity is 0.5–10% as measured with the same method.

As discussed hitherto, the process of firing an unfired layer for the porous ceramic layer of an electrochemical cell is controlled by measuring the electric current flowing between the electrodes or electric voltage present across the electrodes, which current or voltage is varied with the diffusion resistance of the porous ceramic layer which is changed as the firing proceeds. The firing operation is terminated when the detected value of current or voltage corresponds to the predetermined diffusion resistance. Therefore, the instant firing method permits the fired porous ceramic layer of an electrochemical cell to provide a desired diffusion resistance which assures best operating results of the cell, irrespective of cell-to-cell variations in thickness and porosity of the porous ceramic layers, and in surface area of the electrode covered by the porous ceramic layer. Stated differently, the instant method is adapted to detect the diffusion resistance of the porous ceramic layer which is determined by a combination of various factors such as its thickness and porosity, while the firing operation is in progress. Thus, the electrochemical cell with the porous ceramic layer having the accurately controlled diffusion resistance is capable of detecting the concentration of a given component of the measurement gas with improved accuracy.

Further, the method of the invention which permits easy control of the diffusion resistance of the porous ceramic diffusion layer during firing thereof, also contributes to minimization of a variation in the diffusion resistance of the porous ceramic layers from one electrochemical cell to another. Namely, a large number of electrochemical cells produced on a commercial basis according to the instant method will not suffer a variation in their sensing capability. When a batch of cells are fired in one furnace, the firing conditions of the individual cells are different at different locations within the furnace. In the instant method, however, the difference in the firing conditions will not affect the diffusion resistance of the porous ceramic diffusion layer of the cells, because the changing value of the diffusion resistance during the firing operation is monitored by detecting the electric current or voltage which varies with the diffusion resistance, and by terminating the firing operation when the desired diffusion resistance has been reached. For example, the electrochemical cells are automatically taken out of the firing furnace at suitable different timings, at which the predetermined current or voltage corresponding to the desired diffusion resistance has been reached. Accordingly, the electrochemical cells may be produced in a large lot size, with minimum variation in diffusion resistance of their porous ceramic layers, i.e., with increased consistency in quality.

The electrochemical cell manufactured according to the method of the invention may be suitably used for controlling a fuel-rich or fuel-lean exhaust gas emitted from an engine of an automotive vehicle. Further, the electrochemical cell may also be used as an oxygen sensor for determining the oxygen concentration of an exhaust gas which is produced in combustion at the stoichiometric air-fuel ratio. The instant method is also applicable to other sensors or controllers for determining or regulating the concentration of specific components of a fluid associated with electrode reaction, such as nitrogen, carbon dioxide and hydrogen, other than oxygen, and further applicable to humidity sensors using a proton-conductive material.

A few examples are given below to further illustrate the preferred methods of the invention. It is to be understood that these examples are provided for illustrative purpose only, and that the invention is not confined to the precise disclosure of the examples.

EXAMPLE 1

99 parts by weight of powder mixture consisting of 94 mole % of $ZrO_2$ and 6 mole % of $Y_2O_3$ was mixed with 1 part by weight of clay as a sintering aid, 8 parts by weight of polyvinyl butyral as a binder, 4 parts by weight of dioctyl phthalate, and 100 parts by weight of trichloroethylene as a solvent. The mixture was milled in a ball mill, and a slurry was prepared. The slurry was cast, in a conventional doctor-blading process, to form a zirconia green sheet of 0.6 mm thickness, which are cut into rectangular pieces of 10 mm width and 80 mm length, which are used as unfired zirconia layers for the solid electrolyte layer 2, U-shaped spacer 6 and gastight covering plate 4 of the electrochemical cell of FIG. 3.

Figure 6:
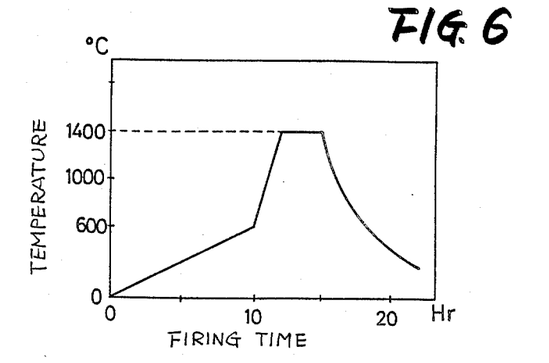
FIGS. 6, 7 and 8 are graphical illustrations showing different temperature-firing time curves used in Examples 1, 2 and 3 of the method of the invention.

On the opposite surfaces of the unfired zirconia layer for the solid electrolyte layer 2, unfired layers for the electrodes 10, 12 were screen-printed as indicated in FIG. 3, by using a paste which was prepared by adding 6 parts by weight of polyvinyl butyral, 3 parts by weight of dibutyl phthalate and 50 parts by weight of butyl carbitol, to a powder mixture which consists of 85% by weight of platinum and 15% by weight of zirconia. The unfired zirconia layer 2 with the screen-printed unfired layers for the electrodes 10, 12, the U-shaped unfired zirconia layer 6 and the unfired zirconia layer 6 are then compacted under heat into an unfired laminar structure. This unfired laminar structure was calcined according to a temperature-time curve of FIG. 6. In this manner, 15 (fifteen) calcined laminar structures were prepared, without the porous ceramic layer 20.

Also, a paste for the porous ceramic layer 20 was prepared by adding 15 parts by weight of polyvinyl butyral, 8 parts by weight of dioctyl phthalate, 1 part by weight of fish oil and 70 parts by weight of butyl carbitol, to 100 parts by weight of powder mixture 70% by weight of $ZrO_2$—$Y_2O_3$ mixture (90 mole% of $ZrO_2$ and 10 mole% of $Y_2O_3$) and 30% by weight of $Al_2O_3$. By using the paste thus prepared, an unfired layer for the porous ceramic diffusion layer 20 was screen-printed on the solid electrolyte layer 2 (calcined zirconia layer) so as to cover the electrode 10.

One of the 15 calcined laminar structures with the unfired layer for the porous ceramic layer 20 was connected to the circuit as shown in FIG. 3, and was heated in the air at 1350° C. for one hour. Subsequently, a voltage is applied between the electrode 12 connected to the positive side of the power source 34, and the electrode 10 connected to the negative side of the power source 34. The current and voltage were read on the ammeter 30 and voltmeter 32. The current was substantially constant at 0.2 V and higher, and the limiting current of 60 mA was obtained at 0.4 V.

Figure 8:
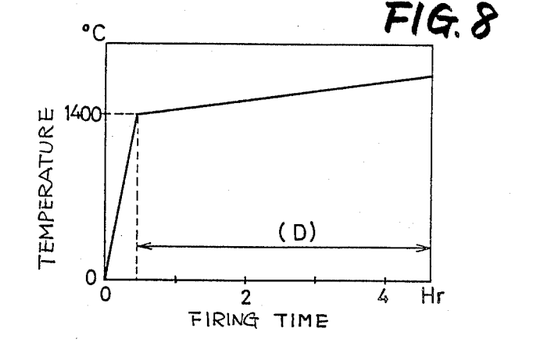
Figure 10:
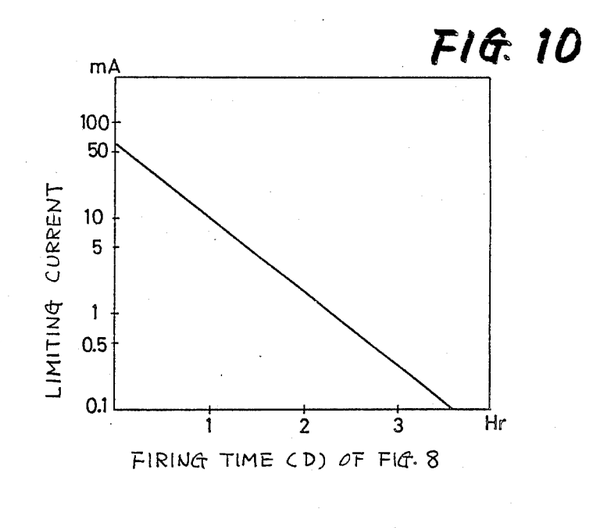

With the electrodes 10, 12 held connected to the power circuit, only the longitudinal end portion of the structure including the electrodes 10, 12 was fired in the air according to a temperature-time curve of FIG. 8. During this firing process, a voltage of 0.4 V was applied between the electrodes 10, 12, and the value of limiting current was monitored by the ammeter 30. As the firing proceeded, the limiting current was changed as shown in FIG. 10.

In the same manner as described above, the remaining 14 (fourteen) calcined laminar structures with the unfired layer for the porous ceramic layer 20 were fired only at their end portions, according to the temperature-time curve of FIG. 8, with the electrodes 10, 12 connected to the power source 34 so that a voltage of 0.4 V was applied therebetween. The firing operation was terminated when the current in the air had been lowered to 15 mA.

The thus obtained 14 electrochemical cells were exposed to a 800° C. flame of an LPG burner with an A/F (air/fuel) ratio of 24. The electrodes 10, 12 were connected to the DC power source 34, and the values of limiting current were measured on the individual cells. The measurements were 6.00±0.02 mA. This result indicates an extremely small variation in the limiting current, i.e., in the diffusion resistance of the porous diffusion layers 20.

EXAMPLE 2

In the same manner as used in EXAMPLE 1, unfired zirconia layers of 10 mm width and 80 mm length were prepared from a zirconia green sheet, which were used for producing the electrochemical cell of FIG. 4.

On the unfired zirconia layer for the solid electrolyte layer 2, unfired layers for the electrodes 10, 14 were screen-printed with the same platinum paste as used in EXAMPLE 1. Further, an unfired layer for the insulating layer 22 was screen-printed on the unfired zirconia layer 2, with an alumina paste which was prepared from 100 parts by weight of alumina mixed with 15 parts by weight of polyvinyl butyral, 8 parts by weight of dioctyl phthalate and 70 parts by weight of butyl carbitol acetate. Further, an unfired layer for the porous ceramic layer 20 and an unfired layer for the electrode 12 were screen-printed with the same pastes as used in EXAMPLE 1. On the surface of the unfired layer 20 on which the unfired layer for the electrode 12 was formed, an unfired layer for a protective layer 24 was screen-printed with the alumina paste used for the insulating layer 22.

On the unfired zirconia layer for the covering plate 4, an unfired layer for the insulating layer 26 was screen-printed with the alumina paste used for the insulating layer 22. A green sheet for a gastight layer 28 was formed of a paste which was prepared from 100 parts by weight of zirconia particles used in EXAMPLE 1, mixed with 8 parts by weight of polyvinyl butyral, 4 parts by weight of dioctyl phthalate and 70 parts by weight of butyl carbitol acetate. On one surface of this green sheet 28, a pattern of the electrical heater 40 was screen-printed with a paste which was prepared by adding 8 parts by weight of polyvinyl butyral, 4 parts by weight of dibutyl phthalate and 50 parts by weight of butyl carbitol acetate, to 100 parts by weight of powder mixture which consists of 90% by weight of platinum and 10% by weight of aluminum.

The unfired laminar sub-structure including the zirconia layer 2, the unfired laminar sub-structure including the zirconia layer 4, and the unfired zirconia layer for the U-shaped spacer 6, are then compacted under heat such that the U-shaped spacer layer 6 is interposed between the two laminar sub-structures. Thus, an unfired laminar structure for the electrochemical cell of FIG. 4 was prepared. This laminar structure was calcined according to the temperature-time curve of FIG. 6. In this manner, 15 (fifteen) calcined laminar structures were produced.

One of the 15 calcined laminar structures was connected to the power soruce 34 as shown in FIG. 4, and a voltage was applied to the electrodes. The current and voltage were read on the ammeter 30 and voltmeter 36. The current was substantially constant at 0.3 V and higher, and the limiting current of 70 mA was obtained at 0.5 V.

Figure 7:
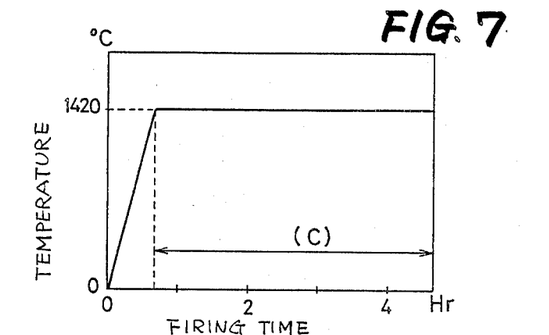

Only the end portion of the same calcined structure was fired according to a temperature-time curve of FIG. 7. The firing operation was interrupted at 15-min. intervals, and the limiting current in the air was measured in each interruption. As the firing proceeded, the limiting current was changed as shown in FIG. 9.

In the same manner as described above, the remaining 14 (fourteen) calcined laminar structures were fired only at their end portions. After 30 minutes, the firing was terminated, and the electrodes 10, 12 were connected to the DC power source 34 to apply 0.5 V between the electrodes. The measurement of the limiting current in the air was 20–30 mA.

Figure 9:
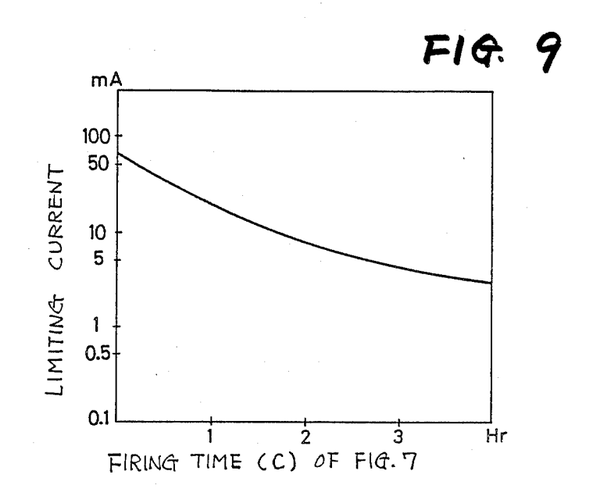
FIGS. 9 and 10 are graphical illustrations showing changes in limiting current of the cell during firing time spans (C) and (D) of FIGS. 7 and 8, respectively.

Based on the temperature-time curve of FIG. 9, a length of time for additional firing of the 14 electrochemical structures (which had been fired for 30 minutes) was estimated, so that the additional firing operation was terminated when the limiting current in the air was lowered to 8 mA. The 14 structures were then fired for the estimated additional time.

The thus obtained 14 electrochemical sensing elements were exposed to a 200° C. flame of an LPG burner with an A/F (air/fuel) ratio of 10. The electrodes 10, 12, 14 were connected to the DC power source 34 with its polarity reversed, and the values of a current flowing through the electrodes 10, 12 were measured on the individual cells at the time when the reading of the voltmeter 36 was 0.3 V. The measurements were 5.00±0.06 mA. This result indicates an extremely small variation in the diffusion resistance of the porous diffusion layers 20.

EXAMPLE 3

Figure 11:
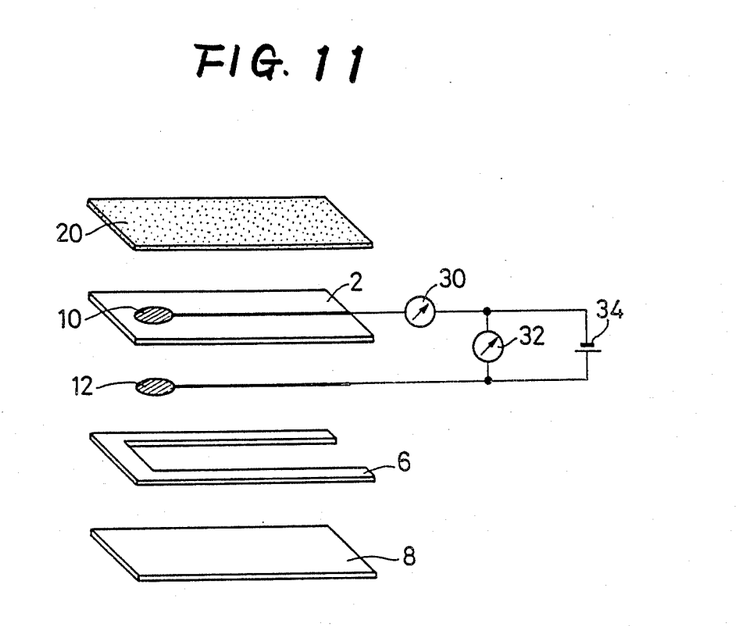
FIG. 11 is an exploded perspective view of an electrochemical cell manufactured according to Example 3 of the method of the invention.

For producing an electrochemical cell of FIG. 11, an alumina substrate 8 was prepared by firing a green sheet at 1600° C., the green sheet being formed of a mixture of 96% by weight of $Al_2O_3$, 3% by weight of $SiO_2$, 1% by weight of CaO and 1% by wight of MgO. For solid electrolyte layers 2, 6, a zirconia paste was prepared by adding 8 parts by weight of polyvinyl butyral, 4 parts by weight of dioctyl phthalate and 70 parts by weight of butyl carbitol, to 100 parts by weight of powder mixture which consists of 96% by weight of $ZrO_2$—$Y_2O_3$ solid electrolyte (95 mole % of $ZrO_2$, 5 mole % of $Y_2O_3$), 2% by weight of $Bi_2O_3$ and 2% by weight of $SiO_2$. For a porous ceramic layer 20, an alumina paste was prepared by adding 20 parts by weight of polyvinyl butyral, 10 parts by weight of dioctyl phthalate and 70 parts by weight of butyl carbitol acetate, to 100 parts by weight of powder mixture consisting of 80% by weight of $Al_2O_3$, 4% by weight of CaO, 4% by weight of MgO, 10% by weight of $SiO_2$ and 2% by weight of $B_2O_3$. On the alumina substrate 8, unfired layers for the solid electrolyte layers 2, 6, porous ceramic layer 20 and electrodes 10, 12 where screen-printed as illustrated in FIG. 11, by using the above-indicated zirconia and alumina pastes, and the platinum paste used in EXAMPLE 1. In this manner, 15 (fifteen) laminar structures for the cell of FIG. 11 were prepared.

The unfired layers for the electrodes 10, 12 were connected to the DC power source 34 as shown in FIG. 11, so that 0.5 V was present between the electrodes 10, 12. The laminar structures were fired at 1000° C., until the current flowing through the electrodes 10, 12 was lowered to 14.3 mA. Thus, the fired laminar structures of the electrochemical sensing elements were produced.

The thus obtained 15 electrochemical sensing elements were exposed to a 600° C. flame of an LPG burner with an A/F (air/fuel) ratio of 23. The electrodes 10, 12 were connected to the DC power source 34, and the values of limiting current flowing through the electrodes 10, 12 were measured on the individual cells. The measurements were 5.80±0.05 mA. This result indicates an extremely small variation in the diffusion resistance of the porous diffusion layers 20.

While the present invention has been described in detail with a certain degree of particularity, it is to be understood that the invention is not confined to the precise disclosure contained herein, but may be otherwise embodied with various changes, modifications and improvements, which may occur to those skilled in the art without departing from the scope of the invention defined in the appended claims.

What is claimed is:

1. A method of manufacturing an electrochemical cell for determining the concentration of a given component of a measurement gas, which has a solid electrolyte body, and at least one pair of electrodes which are disposed on the solid electrolyte body and spaced apart from each other, such that at least one of said at least one pair of electrodes is exposed to the measurement gas via a porous ceramic diffusion layer having a predetermined diffusion resistance to molecules of said component of the measurement gas, so that an atmosphere adjacent to said at least one electrode is controlled by means of reaction at said at least one pair of electrodes by application of an electric current thereto, comprising the steps of:

preparing an unfired or calcined laminar structure of the electrochemical cell such that an unfired or calcined layer of said at least one electrode is covered by an unfired or calcined layer of said porous ceramic diffusion layer;

starting a firing process to fire said unfired or calcined laminar structrure at predetermined elevated temperatures;

applying an electric voltage or current to said at least one pair of electrodes; and terminating said firing process when a value of current flowing through, or voltage present between, said at least one pair of electrodes has become equal to a predetermined value at which is obtained a desired rate of diffusion of said component of the measurement gas through said porous ceramic diffusion layer to said at least one electrode.

2. A method according to claim 1, wherein said value of current or voltage is detected continuously or intermittently, while said unfired or calcined laminar structure of the electrochemical cell is continuously fired.

3. A method according to claim 1, wherein said value of current or voltage is detected at least two times at a temperature lower than a firing temperature at which said unfired or calcined laminer structure of the electrochemical cell is fired, each of said at least two times of detection of said value of current or voltage being effected during interruption of said firing process.

4. A method according to claim 1, wherein said value of current or voltage is detected at least two times, and a point of time at which said predetermined value of the diffusion resistance of the porous ceramic diffusion layer is reached is obtained based on the detected values of current or voltage, said firing process being terminated at the obtained point of time.

* * * * *